United States Patent
Garbagnati et al.

(10) Patent No.: US 6,322,560 B1
(45) Date of Patent: *Nov. 27, 2001

(54) CATHETER FOR RADIOFREQUENCY ABLATION OF TUMORS

(75) Inventors: Francesco Garbagnati, Milan; Sandro Rossi, Piacenza, both of (IT)

(73) Assignee: Thermo-Med 2000 KFT (HU)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/331,834
(22) PCT Filed: Dec. 12, 1997
(86) PCT No.: PCT/IB97/01586
 § 371 Date: Jun. 24, 1999
 § 102(e) Date: Jun. 24, 1999
(87) PCT Pub. No.: WO98/27881
 PCT Pub. Date: Jul. 2, 1998

(30) Foreign Application Priority Data

Dec. 24, 1996 (IT) .............................. MI96A2745

(51) Int. Cl.$^7$ .................................................. A61B 18/18
(52) U.S. Cl. ............................................. 606/41; 607/105
(58) Field of Search ................................. 606/27–31, 41, 606/42; 607/101–105

(56) References Cited

U.S. PATENT DOCUMENTS

| 5,191,883 | * | 3/1993 | Lennox et al. | 606/31 |
| 5,344,435 | * | 9/1994 | Turner et al. | 607/101 |
| 5,431,648 | * | 7/1995 | Lev | 606/27 |
| 5,520,684 | * | 5/1996 | Imran | 606/41 |
| 5,540,679 | * | 7/1996 | Fram et al. | 606/27 |
| 5,545,161 | * | 8/1996 | Imran | 606/41 |
| 5,647,871 | * | 7/1997 | Levine et al. | 606/45 |

\* cited by examiner

*Primary Examiner*—Michael Peffley
(74) *Attorney, Agent, or Firm*—Michael Best & Friedrich LLP

(57) ABSTRACT

A catheter for the treatment of tumors by hyperthermia induced by radiofrequency or other energy comprises a tubular body (1) having a proximal end (2) connected to a handle member and near the other end a cooled metal plate (5) capable to act as active electrode provided with an electric cable (8) for the connection to the energy generator and with thermistors (9, 10) to be connected to the display of the said generator, the tubular body (1) having at least a longitudinal channel (11, 12) for the passage of tissual thermistors, a longitudinal channel for the passage of electric cables and a pair of longitudinal channels for inflow and outflow pipes of the liquid cooling the metal plate (5).

12 Claims, 2 Drawing Sheets

CATHETER FOR RADIOFREQUENCY ABLATION OF TUMORS

FIELD OF THE INVENTION

The present invention relates to a device for the treatment of tumors by hyperthermia induced by radiofrequency or other forms of energy, and in particular to a catheter to be introduced into the human body through natural paths being patent or made patent through their dilation.

BACKGROUND

Tumors of parenchymatous organs or tumors penetrating hollow internal organs are known to be treatable by hyperthermia induced by radiofrequency. Such a treatment is made with suitable radiofrequency generators provided with a passive electrode to be applied outside the patient's body and with an active electrode to be inserted into the patient's body and directly contacting the tumor. The known active electrodes consist of variously sized needles which are inserted into the patient's body by passing them through several layers of the body tissue. This results in drawbacks due to the passing through tissues other than the one to be treated, some of which are not pierceable by large-sized catheters.

From WO 9428809 a transurethral device is already known, which does not require the piercing of tissues other than the one to be treated, but it is limited to the treatment of prostatic hyperplasia and it is not provided with means allowing a real-time monitoring of the temperature of the treated tissue.

WO 96134570 discloses a system for ablating body tissue by hyperthermia using an active electrode which has the shape of a bulb in order to focus the heat on the terminal cap of the bulb-shaped electrode. While this shape of the electrode is appropriate for the treatment of heater tissues, it is no appropriate for the treatment of prostatic hyperplasia where large surfaces of body tissue are to be ablated.

EP 0 629 382 A1 discloses a catheter assembly for the treatment of prostatic hyperplasia wherein the active electrode has the shape of a needle to be driven into the tissue with the drawbacks of the above-mentioned known devices using needles as active electrodes.

The object of the present invention is therefore to provide a device, suitable for the use in thermal ablation of tumors, which is free from the above mentioned drawbacks. Such an object is achieved by the device having the features specified by claim 1, which may be brought in contact or close to the tumor by passing it through natural ways being patent or made patent.

The device according to the present invention has the advantage of being usable in the treatment by hyperthermia of tumors lying in close contact with hollow internal organs, or passed through by hollow internal organs, as well as of tumors penetrating hollow internal organs. For example, the device according, to the present invention may be advantageously used in the treatment of prostatic tumors by passing it through the urethra, of uterus tumors by passing it through the uterine canal, of colangiocarcinoma by passing it through the bile ducts and of pancreas tumors by passing it through the main pancreatic duct.

Another advantage of the device according to the present invention is the fact that it allows to focalize the energy even in very small-sized tissue areas to be treated, whereas in the known devices the needle-shaped active electrodes operate on 360°.

BRIEF DESCRIPTION OF THE DRAWINGS

Further advantages and features of the device according to the present invention will be evident to those skilled in the art from the following detailed description of an embodiment thereof, with reference to the attached drawings, wherein.

DETAILED DESCRIPTION

Figure 1:
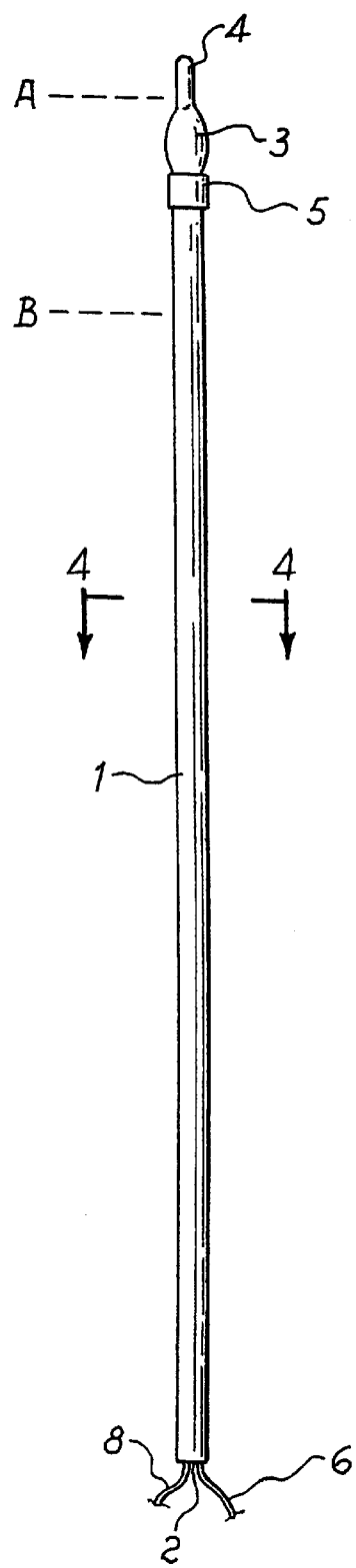
FIG. 1 shows a plan view of a catheter according to the present invention.

Referring to FIG. 1, the catheter according to the present invention may be in form of a common balloon catheter, which comprises in a known way a tubular body 1 having an open end 2 and the opposite end 3 capable of being inflated in a known way so as to form the anchoring balloon intended to adhere inside the bladder. As the Figure shows, besides the portion 3, intended to be inflated as a balloon, tubular body 1 may be advantageously provided with a terminal end 4, usually solid, favouring the introduction of the catheter into a natural path in the patient's organ, e.g. into the urethra. The diameter of tubular body 1 is selected according to the diameter of the patent natural path to be followed. In the case of the urethra it can be of about 7 mm while in the case of oesophagus is of about 3 cm.

In proximity of balloon portion 3, the tubular body 1 has applied thereon a metal plate 5, which acts as the real active electrode of the radiofrequency generator. Such an electrode, when the generator is operated, induces the hyperthermia of the tissue in its proximity and accordingly the necrosis of the tumor lying there. Plate 5 may be made of copper, steel, or any other suitable metal.

Metal plate 5 may extend for 360°, i.e. along the whole circumference of tubular body 1, but it may also extend for only a small portion thereof, e.g. 1–5 degrees. Its position with respect to the opening of the balloon portion 3 must exactly correspond to the distance between the bladder cervix and the prostata. In this way, when the balloon is inflated and expanded inside the bladder, plate 5 will exactly correspond to the cancerous prostata to be treated. In order to allow balloon 3 to be inflated, inside tubular body 1 there is a channel for the passage of a tube 6 connected to an air pump.

The length of plate 5 ranges between 1 mm and 20 cm. Its thickness is comprised between 0.01 mm and 5 mm. The shape of plate 5 may be selected by taking into account that the catheter must easily pass through the paths and possibly allow the flow of organic fluids.

The metal plate 5 can be electrically connected to a radiofrequency generator by means of the cable 8 passing through a longitudinal channel inside the tubular body 1.

Figure 2:
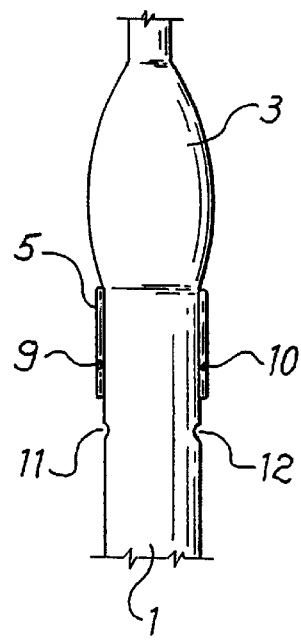
FIG. 2 shows an enlarged view of the detail enclosed between lines A and B of FIG. 1.

Referring to FIG. 2, plate 5 is suitably provided with thermistors 9 and 10 allowing to monitor the temperature inside the plate itself during the use. If necessary, additional thermistors (not shown in the Figure) may be arranged in other points of plate 5. Thermistors 9 and 10 can be electrically connected to a display of the radiofrequency generator by means of wires passing through another longitudinal channel of tubular body 1.

In proximity of plate 5, tubular body 1 has openings 11 and 12 for the passage of other thermistors (not shown), acting so as to monitor the temperature in the treated body tissues. The number of such thermistors, called tissual thermistors, may range from 1 to 4. The tissual thermistors are passed through other longitudinal channels of tubular body 1 and protruded through openings 11 and 12 in order to be positioned in the selected points of the tissues to be treated.

The thermistors are well known so that they do not need a detailed description. The preferred thermistors are the ones available on the market already provided with a very thin electric cable for the required connection with the energy generator. The thermistor is fixed on the tip of a metallic needle with shape memory, while the wire is passed through the cavity of the said needle. The length of the said metallic needle is to be selected in such a way that the portion which protrudes out the relevant openings 11 and 12 has a length of at least 1 cm, preferably in the range from 2 to 4 cm.

The thermistors can be eventually replaced by other similar sensors such as termocouples, resistive wires, optical fibers and so on.

Since the temperature effective for the tumor treatment may result in burns adjacent to sound tissues, such as the urethra, the catheter according to the present invention is suitably provided with a cooling system. In its simplest embodiment such a system consists in water flowing inside plate 1 with the act of a pump suitably connected to the plate.

Figure 3:
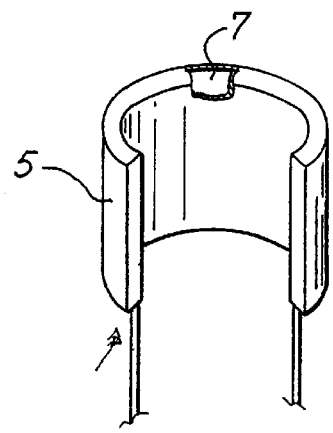
FIG. 3 shows a cooling system of the catheter according to the present invention.

Referring to FIG. 3, the cooling system of plate 5, in its simplest embodiment, comprises a cavity 7 arranged inside the plate itself A cooling fluid, being preferably water, flows through cavity 7 which is provided with an inlet pipe and an outlet pipe for supplying and discharging the cooling fluid, respectively. These pipes are preferably passed through longitudinal channels inside the material forming tubular body 1 of the catheter according to the present invention. The cooling water, directly contacting the metal of plate 5, ensures a constant outward transfer of the heat yielded by the treated tissue to plate 5.

In the embodiment illustrated in FIG. 3 plate 5 has been obtained by bending a metal sheet for giving it the shape of a semicircular closed box provided with inlet and outlet for the cooling liquid. According to another preferred embodiment plate 5 has the shape of a semicilindrical closed box with the diameter almost corresponding to the one of the tubular body 1.

Figure 4:
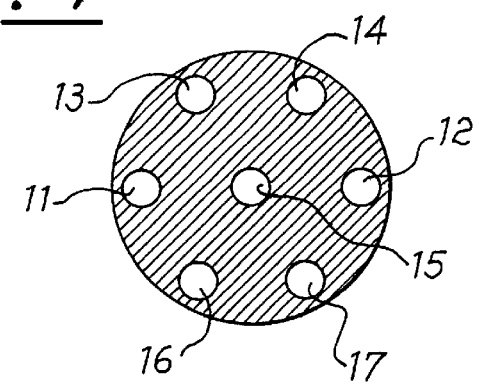
FIG. 4 shows an enlarged cross-sectional plan view taken along line 4—4 of FIG. 1.

FIG. 4 shows the structure of tubular body 1 which is preferably made of plastic material and has a central channel 15 for the passage of a pipe supplying water used to fill the bladder. Channels 11 and 12 are intended for the passage of the tissual thermistors while channels 13 and 14 are intended for the inflow and outflow pipes of the cooling liquid. Channel 16 is intended for the air used for inflating balloon 3 and channel 17 is intended for the passage of cable 8 as well as a cable 32 connecting thermistors 9 and 10 to the displays on the radiofrequency generator.

Plate 5, instead of consisting of a simple metal sheet suitably bent to define the cavity 7, is made of two stamped sheets, so that, when coupled, they form a kind of tube nest or coil improving the cooling efficacy of the liquid circulating inside the plate itself. Plate 5 may consist also of thin pipe helicoidally bent with the coils made adjacent each other.

With a view to better focalize the energy on the tissues to be treated without damaging the surrounding sound tissues, the metal plate 5 is properly sized to surround only one predeterminate fraction of the circumference of tubular body 1. In order to further improve the focalization of the radiofrequency on the tissues to be treated only, a part of the external surface of plate 5 can be covered by a thin layer of an insulating material. The shape of the insulating layer can be selected according to the shape of the tumor to be treated. This is substantial advantage of the catheter device according to the present invention which allows a perfectly dimensioned, sized and shaped active electrode according to the desired focalization of the energy on the tissue to be treated.

The position of plate 5 along the tubular body with respect to the proximal end (2) is to be selected according to the position of the tissue to be treated and the length of the patent natural path available for the treatment.

Figure 5:
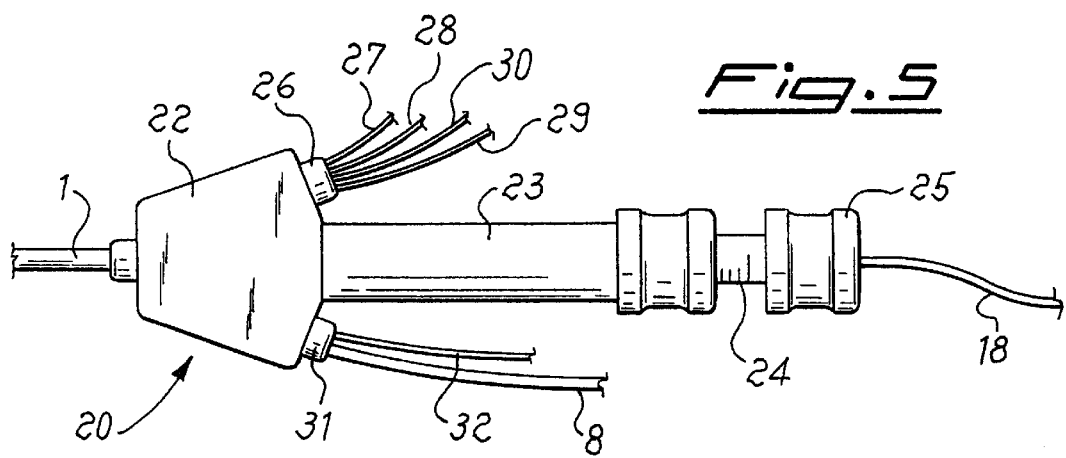
FIG. 5 shows an embodiment of the handle member to be attached to the catheter according to the present invention.

With reference to FIG. 5 the handle member 20 for the catheter device according to the present invention is attached to the tubular body 1 thereof by means of a joining body 22. The joining body 22 has at the opposite side to the one connected to the tubular body 1 a hollow shaft 23 provided with a piston 24 slidable inside the hollow shaft 23. The piston 24 is provided at its proximal extremity with a head 25 which can be easily moved by the operator with the same hand holding the handle member 20. At its distal extremity the piston 24 is provided with at least a tissual thermistor which passes through a longitudinal channel inside tubular body 1 and can go out through the holes 11 and/or 12 for bringing their tips in contact with the more distant areas of the tissue to be reached by the thermal necrosis. Piston 24 is preferably marked with a millimetric scale which allows to exactly monitor the sliding motion of the piston 24 inside the hollow shaft 23 and the resulting movement of the point of thermistor with respect to the tissue to be treated. Piston 24 is provided with an electric cable 18 for connecting the tissual thermistors to the display on the energy generator.

The joining body 22 has an outlet 26 of an internal channel for the passage of the pipes 27 and 28 of the cooling liquid; the pipe 29 for the water used for filling the bladder and the pipe 30 for the air used for inflating the balloon 3.

The handle member 22 is provided with a second outlet 31 of an internal passageway for electric cable 8 as well as for cable 32 connecting the thermistor 9 and 10 to the radiofrequency generator.

Figure 6:
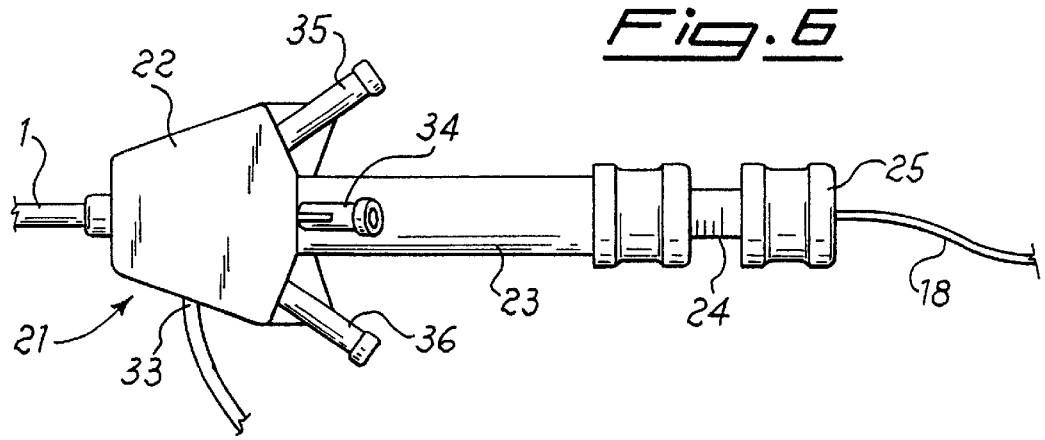
FIG. 6 shows another embodiment of the handle member to be attached to the catheter according to the present invention.

FIG. 6 shows another embodiment 21 of the handle member for a different embodiment of the catheter device according to the present invention, i.e. a catheter without balloon 3 to be used with the aid of a guiding wire or a stylet. In this embodiment we still have a joining body 22 connected to the tubular body 1 and provided with a hollow shaft 23 with its slidable piston 24 bearing at the opposite side of head 25 at least a tissual thermistor which can be pushed through the longitudinal channel 11 or 12 inside the tubular body 1.

The joining body 22 has a lateral outlet 33 for the cables 8 and 32 connecting the active electrode and its thermistors to the radiofrequency generator. A central outlet 34 is for the passage of the guiding wire while the lateral passages 35 and 36 are for the inflow and outflow of the cooling liquid.

When a prostatic tumor is to be treated by hyperthermia the passive electrode of the radiofrequency generator is applied on the patient's back. The catheter according to the present invention is inserted into the urethra until its upper portion lies inside the bladder. Then balloon 3 is inflated by pumping air in pipe 30, which runs along channel 16 inside the tubular body 1 and comes out inside balloon 3. In order to keep the bladder patent, it is finally filled with water which is injected through pipe 29 running along the central channel 15 of the catheter.

A traction and possibly also a torsion is exerted from outside on handle member 20 of the catheter, so as to bring plate 5 to the desired position inside the prostata. The proper position of plate 5 inside the prostata may be controlled by the means usually available such as the rectal echography, the computerized axial tomography or the magnetic resonance. By pushing the head 25 of piston 24 the tissual thermistors are then passed inside tubular body 1 thereby having them protrude from holes 11 and 12 in order to bring their tips exactly in the distal areas of the organ which are to be reached by the desired hyperthermia and subsequent necrosis. After having connected the tissual thermistors to the radiofrequency generator, the ends of the pipes passing through channels 13 and 14 are connected to a pump for circulating the cooling water.

By then, the radiofrequency generator is operated which supplies such a power as to reach and keep a temperature higher than 60° C. in the organ area surrounding the tip of the tissual thermistors. In such conditions, the tissue temperature between plate 5 and the thermistors' tips exceeds 100° C. resulting in the necrosis of the same tissue. These temperatures must be kept for longer than a minute. The radiofrequency generator is then turned off, the thermistors are drawn back inside the catheter, the intravesical balloon is deflated and finally the catheter is removed from the urethra.

In the cases when the catheter according to the present invention must be used in the treatment of other tumors, such as e.g. the colangiocarcinoma, it may lack balloon 3, which in fact acts only so as to anchor the catheter to the bladder cervix. In such a case, the catheter according to the present invention may also lack tip 4, since the catheter can be introduced into the body with the aid of a guiding cable already inserted into the body. For this specific use the embodiment of FIG. 6 is suitably connected to the tubular body 1 and plate 5 with its thermistors, tissual thermistors and cooling system. In such cases, it is neither necessary to remove the catheter after each treatment; in fact, it may be left inside the patient's body, then to be from time to time connected to the radiofrequency generator and to the cooling pump for each subsequent treatment. Such a catheter may be also used for the treatment of pancreas tumors by introducing it through the main pancreatic duct by endoscopy or during surgery.

The catheter according to the present invention may be used with a radiofrequency generator or with a generator of any other suitable energy, such as laser, microwaves and so on. Besides for the thermal ablation of tumors the catheter according to the present invention can be used also for other treatments such as endovascular treatment of atherosclerotic plaques.

What is claimed is:

1. A catheter for the treatment of tumors by hyperthermia induced by an energy generator having a display, the catheter comprising a tubular body having a proximal end connected to a handle member and at a distance therefrom a cooled active electrode provided with an electric cable adapted to be connected to the energy generator, the cooled active electrode being further provided with thermistors adapted to be connected to the display of the generator, characterized in that the tubular body has an internal passage for longitudinal channels and the cooled active electrode includes a metal plate provided with an internal cavity, said cavity at least partially surrounding the tubular body and adapted to receive a flow of coolant therewithin.

2. A catheter according to claim 1, characterized in that said longitudinal channels include at least a longitudinal channel for tissual thermistors, a longitudinal channel for electric cables and a pair of longitudinal channels for the inflow and outflow of a fluid used for cooling the tubular electrode.

3. A catheter according to claim 1, further comprising an inflatable balloon portion located near the distal end of the tubular body, wherein at least one of said longitudinal channels communicates with said balloon portion to facilitate filling said balloon portion with a fluid.

4. A catheter according to claim 3, wherein said balloon is adapted to be at least partially inserted into a bladder of a patient and wherein at least one of said longitudinal channels communicates with the bladder and provides a flow path for water used for filling the bladder.

5. A catheter according to claim 1, characterized in that the tubular electrode extends around the tubular body for 1 to 360°.

6. A catheter according to claim 1, characterized in that the tubular electrode is covered with an insulating material for 1 to 98% of its external surface.

7. A catheter according to claim 2, characterized in that the tubular electrode has an inner cavity communicating with said longitudinal channels supplying the cooling fluid.

8. A catheter according to claim 1, characterized in that the tubular electrode comprises a bent metal sheet.

9. A catheter according to claim 3, characterized in that the handle member comprises a hollow shaft having at one extremity the exit of a slidable piston bearing at its proximal end an electric cable and at its distal end a tissual thermistor, and at the opposite extremity a joining body having internal passages communicating at one side with the hollow shaft and at the opposite side with the tubular body, said joining body being provided with internal passageways communicating with said longitudinal channels of said tubular body, a first outlet for a fluid for cooling the tubular electrode, water used to fill a bladder, and the fluid used to inflate the balloon portion, and a second outlet for at least one of said electric cables.

10. A catheter according to claim 1, characterized in that the handle member comprises a hollow shaft having at one extremity the exit of a slidable piston bearing at its proximal end an electric cable and at its distal end at least a tissual thermistor, and at the opposite extremity a joining body communicating at one side with the hollow shaft and at the opposite side with the tubular body; said joining body being provided with internal passageways, an outlet for electric cables, an outlet for one of a stylet and a guiding wire, and outlets for circulating a cooling liquid for cooling the active electrode.

11. A catheter of claim 1, wherein said metal plate includes first and second nested walls defining said cavity therebetween.

12. A catheter of claim 11, wherein said first and second walls are integrally cast with each other.

* * * * *